United States Patent
Park et al.

(10) Patent No.: US 11,278,227 B2
(45) Date of Patent: Mar. 22, 2022

(54) BIOMETRIC INFORMATION MEASUREMENT METHOD AND BIOMETRIC INFORMATION MEASUREMENT SYSTEM

(71) Applicant: Electronics and Telecommunications Research Institute, Daejeon (KR)

(72) Inventors: Young Sam Park, Daejeon (KR); Jaehyun Moon, Daejeon (KR); Seongdeok Ahn, Daejeon (KR); Byoung Gon Yu, Chungcheongbuk-do (KR); Jeong Ik Lee, Daejeon (KR); Nam Sung Cho, Daejeon (KR); Doo-Hee Cho, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 178 days.

(21) Appl. No.: 16/566,092

(22) Filed: Sep. 10, 2019

(65) Prior Publication Data

US 2020/0107739 A1    Apr. 9, 2020

(30) Foreign Application Priority Data

Oct. 5, 2018  (KR) .................. 10-2018-0119354
Feb. 22, 2019 (KR) .................. 10-2019-0021455

(51) Int. Cl.
*A61B 5/25*     (2021.01)
*G06K 9/00*     (2022.01)
(Continued)

(52) U.S. Cl.
CPC ............. *A61B 5/25* (2021.01); *A61B 5/053* (2013.01); *G01N 33/4836* (2013.01);
(Continued)

(58) Field of Classification Search
CPC ......... G01N 33/4833; G01N 33/48707; G01N 33/48728; A61B 5/25; A61B 5/053; G06K 9/00885

See application file for complete search history.

(56) References Cited

U.S. PATENT DOCUMENTS

| | | | |
|---|---|---|---|
| 5,030,333 A | * | 7/1991 | Clark, Jr. ........... G01N 27/3271 205/777.5 |
| 7,783,334 B2 | | 8/2010 | Nam et al. |
| 8,724,855 B2 | | 5/2014 | Kim |

FOREIGN PATENT DOCUMENTS

| KR | 10-2011-0049321 A | 5/2011 |
|---|---|---|
| KR | 10-2018-0096295 A | 8/2018 |

OTHER PUBLICATIONS

By Lowry et al., "Measurement of brain tissue oxygen at a carbon past electrode can serve as an index of increases in regional cerebral blood flow," Journal of Neuroscience Methods 71 (1997) 177-182 (Year: 1997).*

(Continued)

*Primary Examiner* — Alexander S Noguerola
(74) *Attorney, Agent, or Firm* — Rabin & Berdo, P.C.

(57) ABSTRACT

Provided is a biometric information measurement method. The method includes providing a bio-material including at least one of cells and tissues, contacting a first electrode and a second electrode with the bio-material and applying a first electrical signal and a second electrical signal to the bio-material, sensing a third electrical signal from the bio-material, and analyzing an oxygen concentration in the bio-material from the third electrical signal.

9 Claims, 12 Drawing Sheets

(51) Int. Cl.
*G01N 33/50* (2006.01)
*A61B 5/053* (2021.01)
*G01N 33/483* (2006.01)
*A61B 5/00* (2006.01)

(52) U.S. Cl.
CPC ......... *G01N 33/50* (2013.01); *G06K 9/00885* (2013.01); *A61B 5/742* (2013.01)

(56) References Cited

OTHER PUBLICATIONS

Crile et al., "The Electrical Conductivity of Amical Tissues under Normal and Pathological Conditions,"American Journal of Physiology, vol. 60, issue 1, Mar. 1922, pp. 59-106 (Year: 1922).*
Gabriel et al., "Final Report for the Period d Dec. 15, 1994-Dec. 14, 1995", Prepared for AFOSR/NL Bolling AFB DC 20332-0001, Jun. 1996 (Year: 1996).*
Gun et al., "Effective Permittivity of Biological Tissue: Comparison of Theoretical Model and Experiment," Hindawi Mathematical Problems in Engineering, vol. 2017, Article ID 7249672, 7 pages (Year: 2017).*
Arati Sridharan, et al., "Assessing Brain Tissue Oxygenation at Interfaces Using a Novel MR Imaging Approach", 2018 MRS Spring Meeting, Apr. 4, 2018.

* cited by examiner

BIOMETRIC INFORMATION MEASUREMENT METHOD AND BIOMETRIC INFORMATION MEASUREMENT SYSTEM

CROSS-REFERENCE TO RELATED APPLICATIONS

This U.S. non-provisional patent application claims priority under 35 U.S.C. § 119 of Korean Patent Application Nos. 10-2018-0119354, filed on Oct. 5, 2018, and 10-2019-0021455, filed on Feb. 22, 2019, the entire contents of which are hereby incorporated by reference.

BACKGROUND

The present disclosure herein relates to a biometric information measurement method and a biometric information measurement system.

Recently, brain science study has been actively conducted. Brain science research is focused on the treatment of damaged nerve cells using electrical or optical stimuli. Like normal cells, nerve cells receive oxygen into a cell, simultaneously consuming oxygen in the cell and producing energy while producing carbon dioxide. The carbon dioxide produced in the cell is released to the outside of the cell.

Since oxygen consumption and carbon dioxide production in cells, the basic unit of life, are the most fundamental phenomenon that determines the fate of life, a scientific understanding of this is needed.

SUMMARY

The present disclosure provides a biometric information measurement method with improved accuracy and reliability and a biometric information measurement system used therefor.

An embodiment of the inventive concept provides a biometric information measurement method including: providing a bio-material including at least one of cells and tissues; contacting a first electrode and a second electrode with the bio-material and applying a first electrical signal and a second electrical signal to the bio-material; sensing a third electrical signal from the bio-material; and analyzing an oxygen concentration in the bio-material from the third electrical signal.

In an embodiment, the first electrical signal may include a current or a voltage, wherein the second electrical signal may include a current or a voltage.

In an embodiment, the third electrical signal may include permittivity or electrical conductivity.

In an embodiment, the method may further include injecting markers in the bio-material, wherein the injecting of the markers may be performed before applying the first electrical signal and the second electrical signal.

In an embodiment, the injecting of the markers may be performed through an injector.

In an embodiment, the injecting of the makers may be performed through the first electrode.

In an embodiment, the first electrode may have an injection unit therein, and the markers may be provided in the injection unit.

In an embodiment, the injecting of the markers may be performed using the second electrode.

In an embodiment, the contacting of the first electrode with the bio-material may include penetrating a surface of the bio-material.

In an embodiment, the method may further include contacting a third electrode with the bio-material, wherein the sensing of the third electrical signal may be performed through the third electrode.

In an embodiment, the method may further include: contacting a fourth electrode with the bio-material; and sensing a fourth electrical signal from the bio-material through the fourth electrode, wherein the fourth electrical signal may be different from the third electrical signal.

In an embodiment, the fourth electrical signal may include permittivity or electrical conductivity.

In an embodiment of the inventive concept, a biometric information measurement system includes a biometric information measurement device including: a control unit including a signal applying unit and a signal receiving unit; a first electrode electrically connected to the signal applying unit and the signal receiving unit; and a second electrode electrically connected to the signal applying unit and the signal receiving unit, wherein the first electrode applies a first electrical signal to a bio-material, wherein the second electrode applies a second electrical signal to the bio-material, wherein the signal receiving unit collects a third electrical signal generated from the bio-material.

In an embodiment, the signal receiving unit may collect the third electrical signal through the first electrode and the second electrode, wherein the signal applying unit may apply the first electrical signal and the second electrical signal through the first electrode and the second electrode.

In an embodiment, the control unit may further include a signal analyzing unit, wherein the signal analyzing unit may analyze an oxygen concentration in the bio-material from the third electrical signal.

In an embodiment, the system may further include a biometric information analyzing unit spaced apart from the biometric information measurement device, wherein the biometric information analyzing unit may analyze an oxygen concentration in the bio-material from the third electrical signal.

In an embodiment, the first electrode and the second electrode may be configured to contact the bio-material.

In an embodiment, the first electrical signal may include a current or a voltage, wherein the second electrical signal may include a current or a voltage, wherein the third electrical signal may include permittivity or electrical conductivity.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Hereinafter, preferred embodiments of the inventive concept will be described in detail with reference to the accompanying drawings. Advantages and features of the inventive concept, and implementation methods thereof will be clarified through following embodiments described with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art and the inventive concept is only defined by the scope of the claims.

The terms used in this specification are used only for explaining specific embodiments while not limiting the inventive concept. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components. In addition, since they are in accordance with the preferred embodiment, the reference numerals shown in the order of description are not necessarily limited to the order. In addition, in this specification, when a film is referred to as being on another film or substrate, it may be directly formed on another film or substrate, or a third film may be interposed therebetween.

Although the terms first, second, third, etc. have been used in various embodiments herein to describe components (or structures) and the like, it should be understood that these regions and layers are not limited to the terms. These terms are merely used to distinguish predetermined components (or structures) from other components (or structures). Accordingly, the component referred to as a first structure in any one embodiment may be referred to as a second structure in other embodiments. Embodiments described herein include complementary embodiments thereof. Like reference numerals refer to like components throughout the specification.

Additionally, embodiments described in this specification will be described with plan views and sectional views, that is, ideal exemplary views of the inventive concept. In the drawings, the thicknesses of a layer and an area are exaggerated for effective description. Accordingly, shapes of the exemplary views may be modified according to manufacturing techniques and/or allowable errors. Therefore, the embodiments of the inventive concept are not limited to the specific shape illustrated in the exemplary views, but may include other shapes that may be created according to manufacturing processes. For example, an etched region illustrated as a rectangle may have rounded or curved features. Areas exemplified in the drawings have general properties, and are used to illustrate a specific shape of a semiconductor package region. Thus, this should not be construed as limited to the scope of the inventive concept.

Biometric information systems according to the inventive concept are described.

Figure 1A:
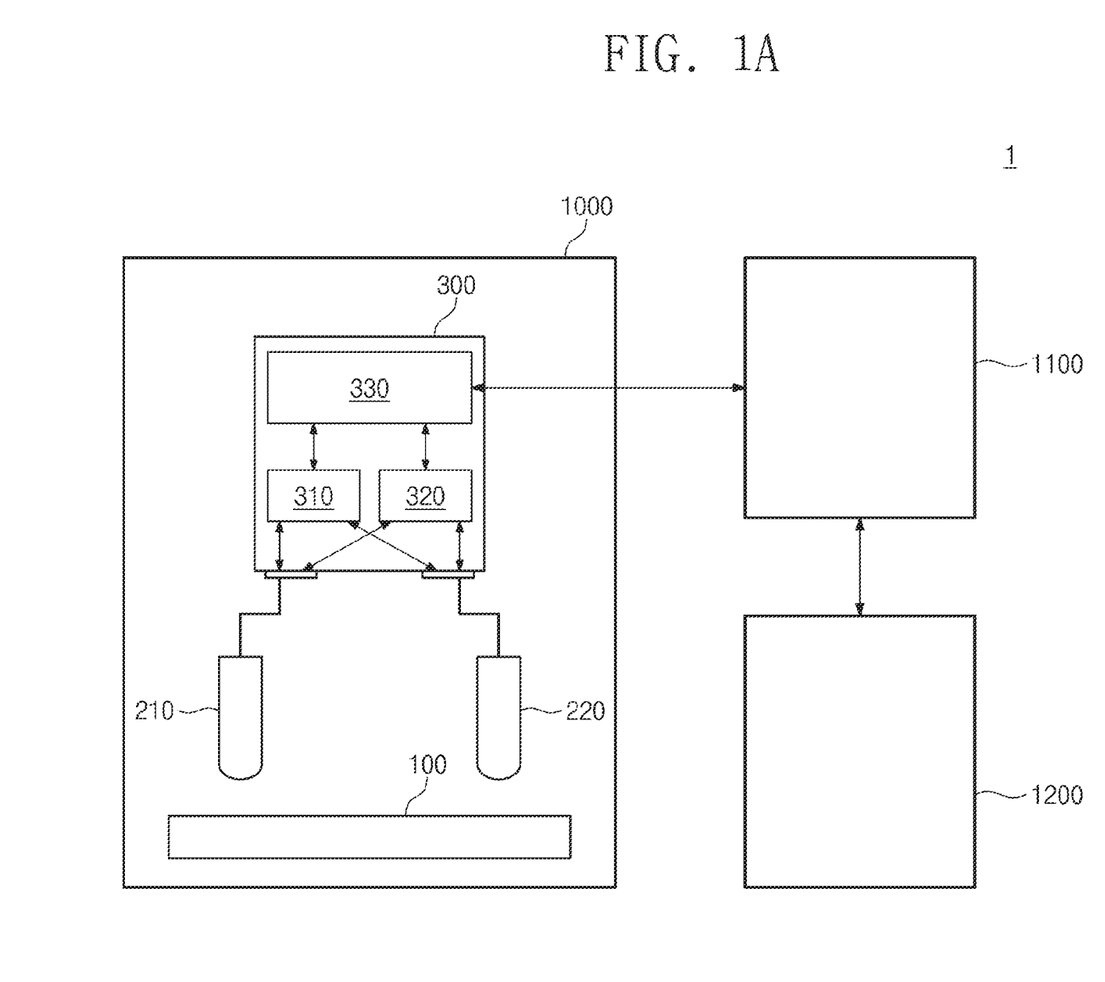
FIG. 1A is a schematic diagram illustrating a biometric information measurement system according to an embodiment.

FIG. 1A is a schematic diagram illustrating a biometric information measurement system according to an embodiment.

Figure 1B:
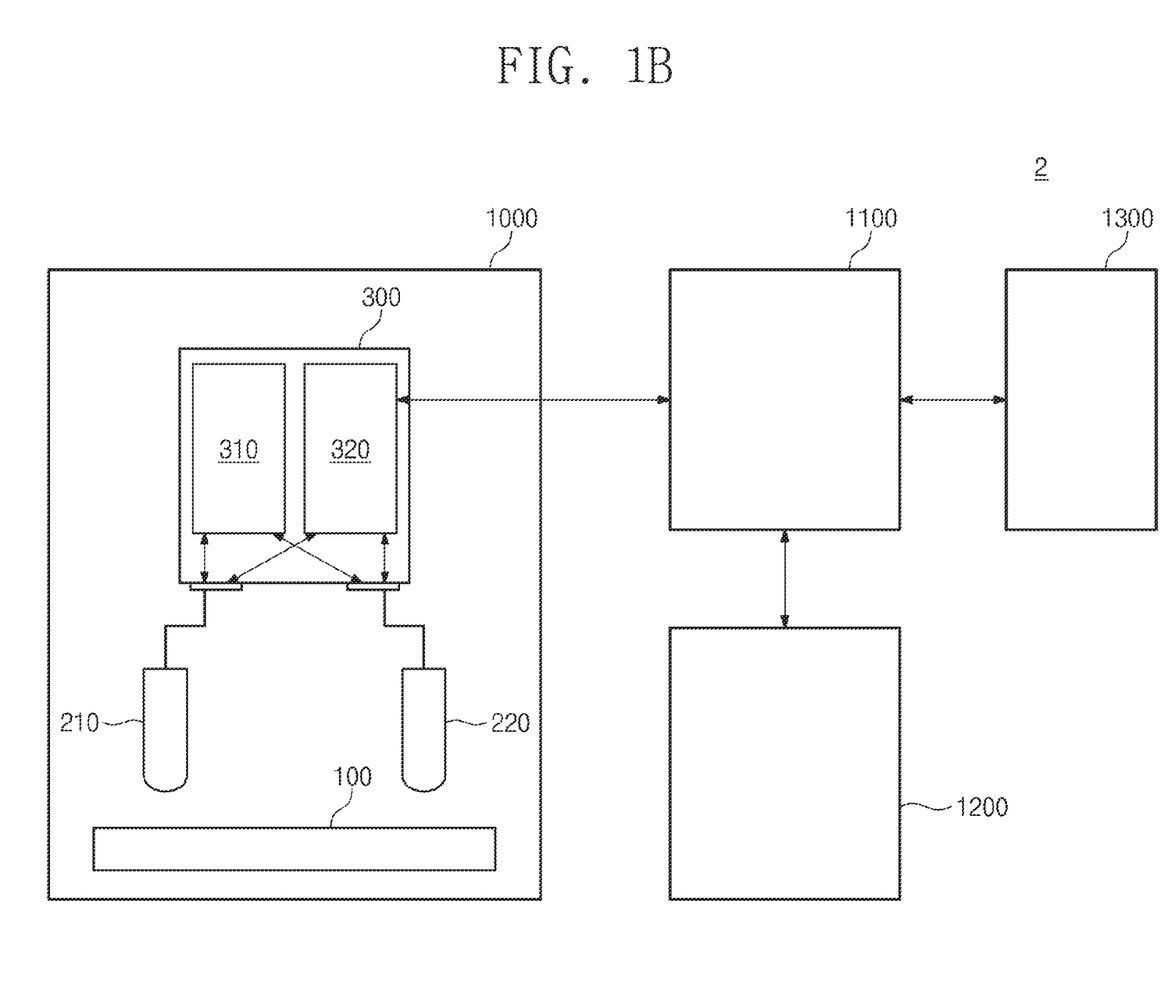
FIG. 1B is a schematic diagram illustrating a biometric information measurement system according to another embodiment.

Referring to FIG. 1A, a biometric information measurement system 1 may include a biometric information measurement device 1000. The biometric information measurement device 1000 may include a plate 100, a first electrode 210, a second electrode 220, and a control unit 300. The first electrode 210 and the second electrode 220 may be provided on the plate 100. The control unit 300 may include a signal applying unit 310, a signal receiving unit 320, and a signal analyzing unit 330. The signal applying unit 310 may be electrically connected to the first electrode 210 and the second electrode 220. The arrows in FIGS. 1A and 1B schematically show the electrical connection in the control unit 300. The signal applying unit 310 may determine whether or not to apply an electrical signal to the first electrode 210 and the second electrode 220. The signal applying unit 310 may further control the type and intensity of the electrical signal applied to the first electrode 210 and the second electrode 220. The signal receiving unit 320 may be electrically connected to the first electrode 210 and the second electrode 220. The signal receiving unit 320 may collect electrical signals sensed by the first electrode 210 and the second electrode 220.

The signal analyzing unit 330 may be electrically connected to the signal applying unit 310 and the signal receiving unit 320. The signal analyzing unit 330 may compare and analyze the electrical signals applied in the signal applying unit 310 and the electrical signals collected in the signal receiving unit 320. Accordingly, the signal analyzing unit 330 may provide information on the living body. The biometric information may be information on the oxygen concentration.

The biometric information measurement system 1 may further include an information transmitting/receiving unit 1100 and a display unit 1200. The information transmitting/receiving unit 1100 may be electrically connected to the control unit 300. More specifically, the information transmitting/receiving unit 1100 may be electrically connected to the signal analyzing unit 330 to receive the biometric information analyzed by the signal analyzing unit 330. In one example, the information transmitting/receiving unit 1100 may be spaced apart from the biometric information measurement device 1000. As another example, the information transmitting/receiving unit 1100 may be integrated with the biometric information measurement device 1000. In this case, the information transmitting/receiving unit 1100 may be provided in the control unit 300.

The information transmitting/receiving unit 1100 may transmit the biometric information to the display unit 1200. The display unit 1200 may display the biometric information. The display unit 1200 may include a display element such as a liquid crystal display (LCD) element, a field emission display (FED) element, a plasma display panel (PDP) element, or an organic light emitting diode element.

The biometric information analyzed in the control unit 300 may be transmitted to an external device through an information transmitting/receiving unit 1100. For example, the information transmitting/receiving unit 1100 may include a wired or wireless communication module capable of Bluetooth, Near Field Communication (NFC), ZigBee, Wi-Fi, USB, or serial communication. The external device may include a cellular phone, a smart watch, a tablet computer, a notebook, or a personal computer. The biometric information analyzed in the biometric information measurement device 1000 may be displayed on various external devices without any spatial limitation. For example, the presence and concentration of the biomaterial may be displayed on the display unit 1200 of the personal mobile phone. In this case, the display unit 1200 may be spaced apart from the biometric information measurement device 1000. As another example, the biometric information measurement device 1000 may be connected to the hospital network system through the information transmitting/receiving unit 1100. Accordingly, the user may receive healthcare services such as remote health monitoring.

FIG. 1B is a schematic diagram illustrating a biometric information measurement system according to another embodiment.

Referring to FIG. 1B, the biometric information measurement system 2 may include a biometric information measurement device 1000, an information transmitting/receiving unit 1100, and a biometric information analyzing unit 1300. The biometric information measurement device 1000 may include a plate 100, a first electrode 210, a second electrode 220, and a control unit 300. The control unit 300 may include a signal applying unit 310 and a signal receiving unit 320. The signal applying unit 310 and the signal receiving unit 320 may be substantially the same as those described with reference to FIG. 1A. However, the control unit 300 may not include the signal analyzing unit 330 of FIG. 1A. An electrical signal sensed by the first electrode 210 and the second electrode 220 may be transmitted to the information transmitting/receiving unit 1100 through the signal receiving unit 320.

The electrical signal received at the information transmitting/receiving unit 1100 may be transmitted to the biometric information analyzing unit 1300. The biometric information analyzing unit 1300 may compare and analyze the electrical signals applied in the signal applying unit 310 and the electrical signals collected in the signal receiving unit 320. For example, the biometric information analyzing unit 1300 may compare and analyze the electrical signals applied to the first electrode 210 and the second electrode 220 and the electrical signals sensed by the first electrode 210 and the second electrode 220. Accordingly, the biometric information analyzing unit 1300 may provide information on the living body. The biometric information analyzing unit 1300 may be spaced apart from the biometric information measurement device 1000. The biometric information analyzing unit 1300 may be an information processing system of the user (for example, a mobile phone, a smart watch, a tablet computer, or a notebook) or an information processing system of a hospital. Since the biometric information analyzing unit 1300 is used, biometric information may be analyzed through various computers or systems.

The biometric information measurement system 2 may further include a display unit 1200 as described with reference to FIG. 1A.

A biometric information measurement device according to the concept of the inventive concept and a biometric information measurement method using the same will be described. In the following descriptions of FIGS. 2 to 11, FIGS. 1A and 1B are referenced together and described.

Figure 2:
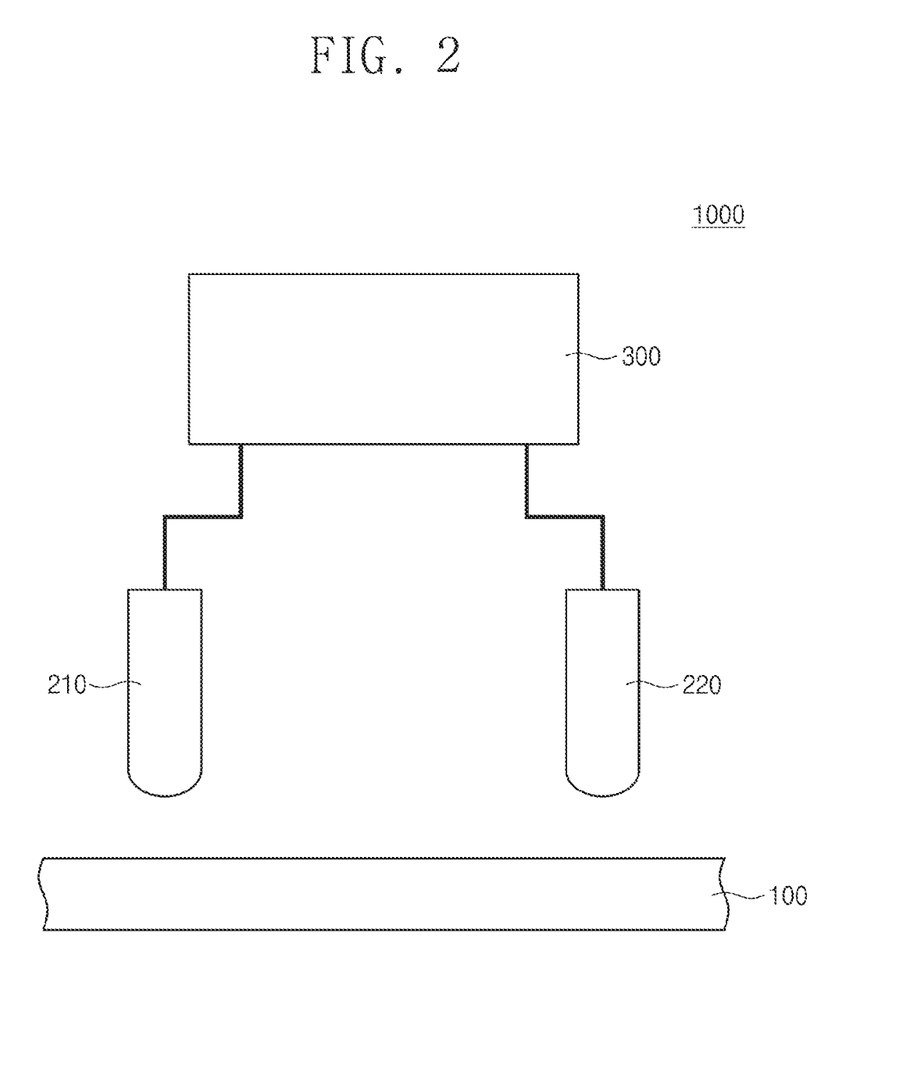
FIG. 2 is a schematic diagram illustrating a biometric information measurement device according to embodiments.
Figure 3:
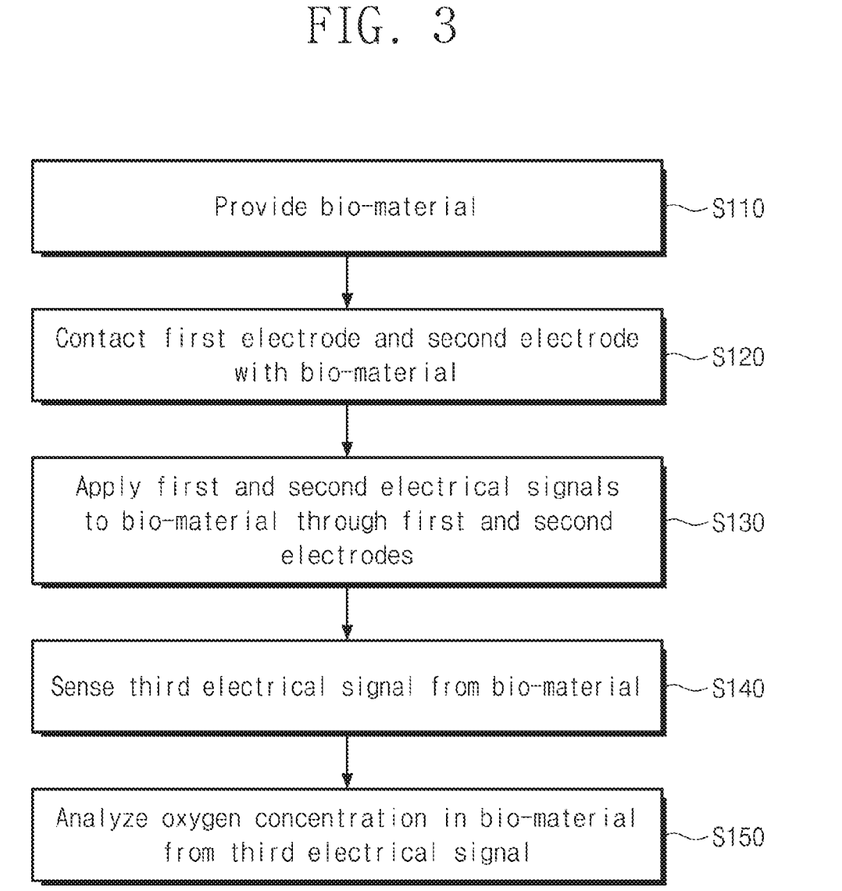
FIG. 3 is a flowchart illustrating a biometric information measurement method according to an embodiment.
Figure 4:
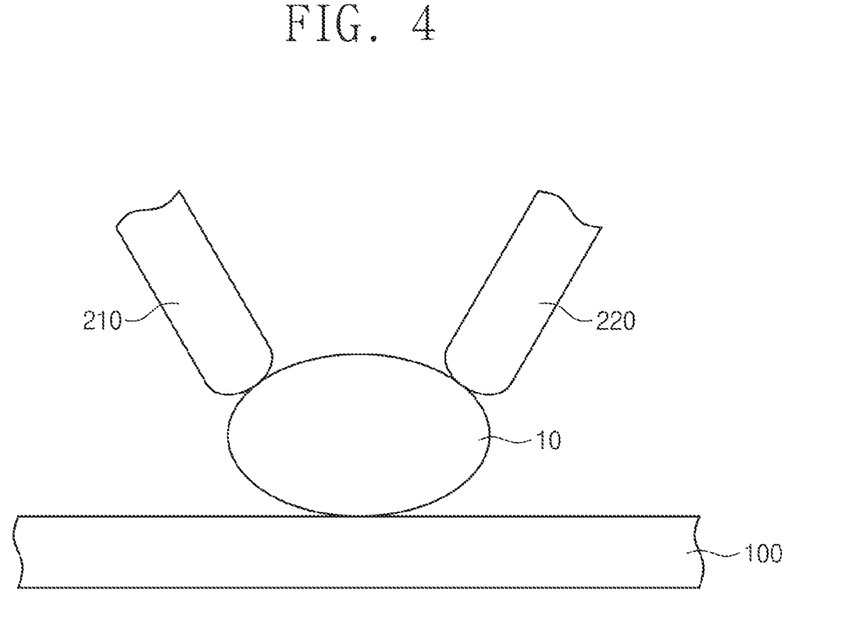
FIG. 4 is a diagram for explaining a biometric information measurement method according to an embodiment.

FIG. 2 is a schematic diagram illustrating a biometric information measurement device according to an embodiment. FIG. 3 is a flowchart illustrating a biometric information measurement method according to an embodiment. FIG. 4 is a diagram for explaining a biometric information measurement method according to an embodiment.

Referring to FIGS. 2, 3 and 4, a biometric information measurement device 1000 may include a plate 100, a first electrode 210, a second electrode 220, and a control unit 300. The biometric information may be information on the oxygen concentration. The first electrode 210 and the second electrode 220 may be provided on the plate 100. The first electrode 210 and the second electrode 220 may include a conductive material. The first electrode 210 may function as a sensing electrode and a driving electrode. The second electrode 220 may function as a sensing electrode and a driving electrode. The driving electrode may refer to an electrode that applies an electrical signal to the component. The sensing electrode may refer to an electrode that senses an electrical signal from the component. The control unit 300 may be electrically connected to the first electrode 210 and the second electrode 220.

The bio-material 10 may be provided as shown in FIGS. 3 and 4 (S110). For example, the bio-material 10 may be provided on the plate 100. The bio-material 10 may be at least one of a cell and a tissue.

The first electrode 210 and the second electrode 220 may be in contact with the bio-material 10 (S120). According to an embodiment, the fact that the first electrode 210 is in contact with the bio-material 10 may include a case where the first electrode 210 is in physical contact with the surface of the bio-material 10. At this time, the first electrode 210 may not penetrate the surface of the bio-material 10. According to another example, the fact that the first electrode 210 contacts the bio-material 10 may include a case where the first electrode 210 penetrates at least a portion of the bio-material 10, for example, the surface of the bio-material 10. The fact that the second electrode 220 contacts the bio-material 10 may include a case where the second electrode 220 physically contacts the surface of the bio-material 10 but does not penetrate the surface of the bio-material 10. As another example, the fact that the second electrode 220 contacts the bio-material 10 may include penetrating the surface of the bio-material 10.

The first and second electrical signals may be applied to the bio-material 10 through the first electrode 210 and the second electrode 220 (S130). For example, the first electrical signal may be applied to the material 10. The second electrode 220 may apply a second electrical signal to the bio-material 10. The application of the first electrical signal may include application of a current or voltage. The application of the second electrical signal may include application of a current or voltage. As another example, the first electrode 210 or the second electrode 220 may apply an optical signal such as an electromagnetic wave to the bio-material 10. The signal applying unit 310 may determine the operation of the first electrode 210 and the first electrical signal applied to the first electrode 210. The signal applying unit 310 may determine the operation of the second electrode 220 and the second electrical signal applied to the second electrode 220. The second electrical signal may be different from the first electrical signal.

The third electrical signal may be sensed from the bio-material 10 through at least one of the first electrode 210 and the second electrode 220 (S140). The third electrical signal may be related to the difference between the first electrical signal and the second electrical signal and the oxygen concentration in the bio-material 10. For example, if the first electrical signal is a first voltage and the second electrical signal is a second voltage, the third electrical signal may include a difference between the first voltage and the second voltage and a change value of the voltage difference due to the oxygen concentration in the bio-material 10. The third electrical signal may be permittivity or electrical conductivity. The third electrical signal may be collected in the signal receiving unit 320. The third electrical signal collected at the signal receiving unit 320 may be transmitted to the signal analyzing unit 330 of FIG. 1A or the biometric information analyzing unit 1300 of FIG. 1B.

The oxygen concentration in the bio-material 10 may be analyzed from the third electrical signal (S150). The signal analyzing unit 330 of FIG. 1A or the biometric information analyzing unit 1300 of FIG. 1B may analyze the third electrical signal to measure the oxygen concentration in the bio-material 10. By analyzing the third electrical signal, the oxygen concentration in the bio-material 10 may be measured quantitatively. The oxygen concentration of the bio-material 10 may determine whether the bio-material 10 is normal or abnormal. For example, the oxygen concentration of an abnormal bio-material may be different from the oxygen concentration of a normal bio-material. The abnormal bio-material may be a bio-material related to the disease. Thus, early detection of diseases such as cancer, brain disease, and heart disease may be possible.

As an example, the oxygen concentration measurement of the bio-material 10 may be performed continuously or consecutively. Thus, a change in the oxygen concentration in the bio-material 10 may be analyzed.

Figure 5:
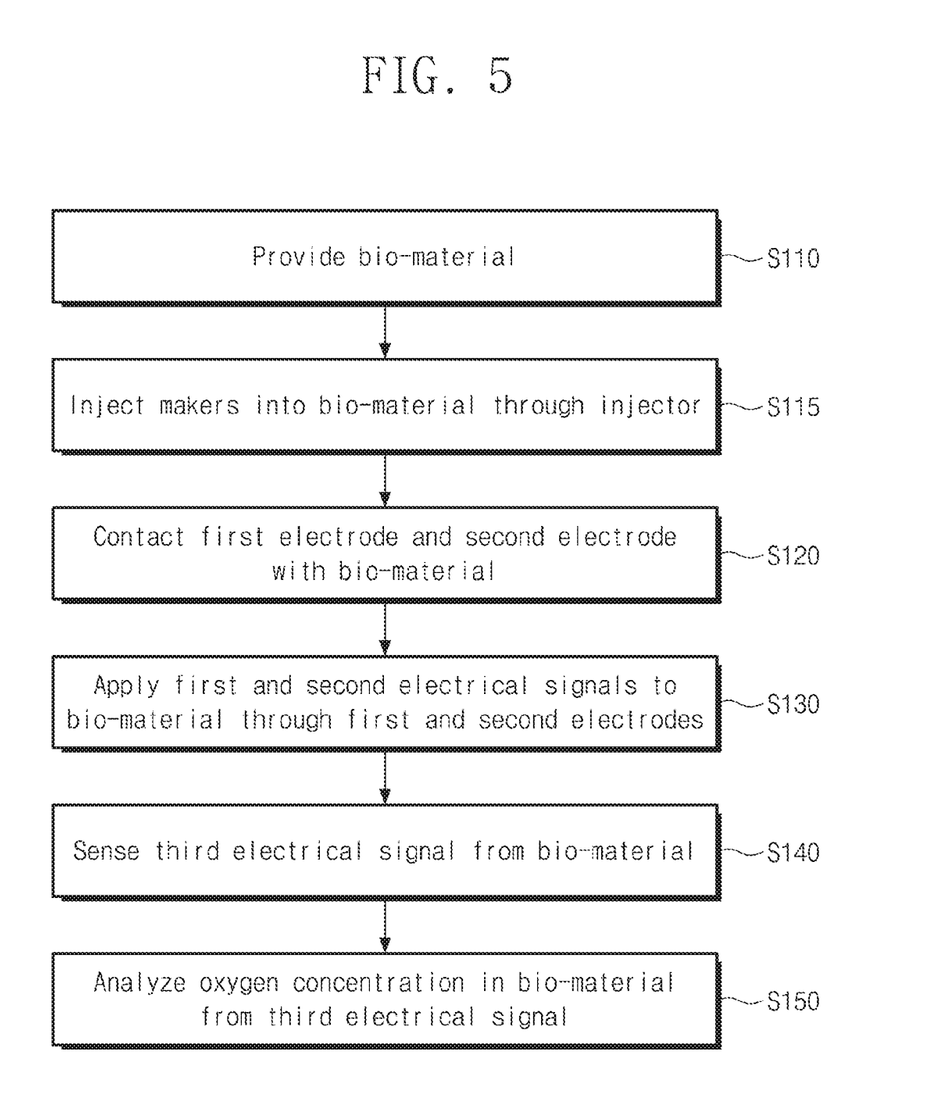
FIG. 5 is a flowchart illustrating a biometric information measurement method according to another embodiment.
Figure 6A:
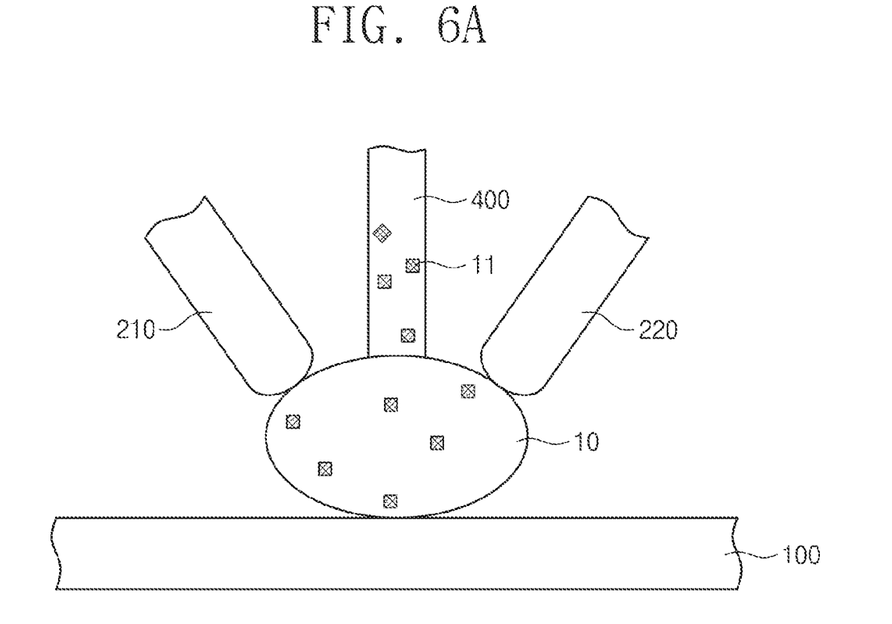
FIGS. 6A and 6B are diagrams for explaining a biometric information measurement method according to another embodiment.
Figure 6B:
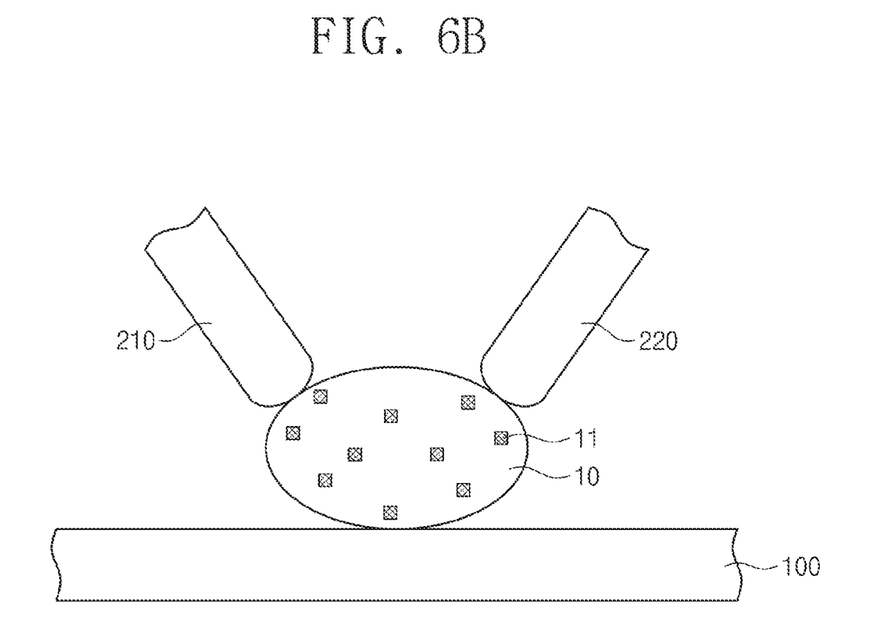

FIG. 5 is a flowchart illustrating a biometric information measurement method according to another embodiment. FIGS. 6A and 6B are diagrams for explaining a biometric information measurement method according to another embodiment. The following description will be made with reference to FIG. 2, and the contents overlapping with those described above will be omitted.

Referring to FIGS. 2, 5, 6A, and 6B, the biometric information measurement method of bio-material 10 may include providing the bio-material 10 (S110), injecting markers 11 into the bio-material 10 through the injector 400 (S115), contacting the first electrode 210 and the second electrode 220 with the bio-material 10 (S120), applying first and second electrical signals to the bio-material 10 through the first and second electrodes 210 and 220 (S130), sensing a third electrical signal from the bio-material 10 (S140), and measuring the oxygen concentration in the bio-material 10 from the third electrical signal (S150). The providing of the bio-material 10 (S110), the contacting of the first electrode 210 and the second electrode 220 with the bio-material 10 (S120), the applying of the first and second electrical signals to the bio-material 10 through the first and second electrodes 210 and 220 (S130), the sensing of the third electrical signal from the bio-material 10 (S140), and the measuring of the oxygen concentration in the bio-material 10 from the third electrical signal (S150) are substantially the same as those described with reference to FIGS. 2 to 4.

Referring to FIGS. 2, 5 and 6A, the markers 11 may be provided in the injector 400. The injector 400 may penetrate the surface of the bio-material 10. The markers 11 may be provided in the bio-material 10 through the injector 400. Thereafter, the injector 400 may be removed.

Injecting the markers 11 into the bio-material 10 through the injector 400 (S115) may be accomplished before contacting the first electrode 210 and the second electrode 220 with the bio-material 10 (S120). Unlike what is shown in the drawings, the injecting of the markers 11 into the bio-material 10 through the injector 400 (S115) may be accomplished after the contacting of the first electrode 210 and the second electrode 220 with the bio-material 10 (S120).

Referring to FIGS. 2, 5, and 6B, after the injecting of the markers 11 into the bio-material 10 through the injector 400 (S115), applying the first and second electrical signals to the bio-material 10 through the first and second electrodes 210 and 220 (S130) may be performed.

When the markers 11 are provided in the bio-material 10, permittivity or electrical conductivity generated in the bio-material 10 by the markers 11 may be changed. The third electrical signal may depend on the oxygen concentration in the bio-material 10.

Figure 7:
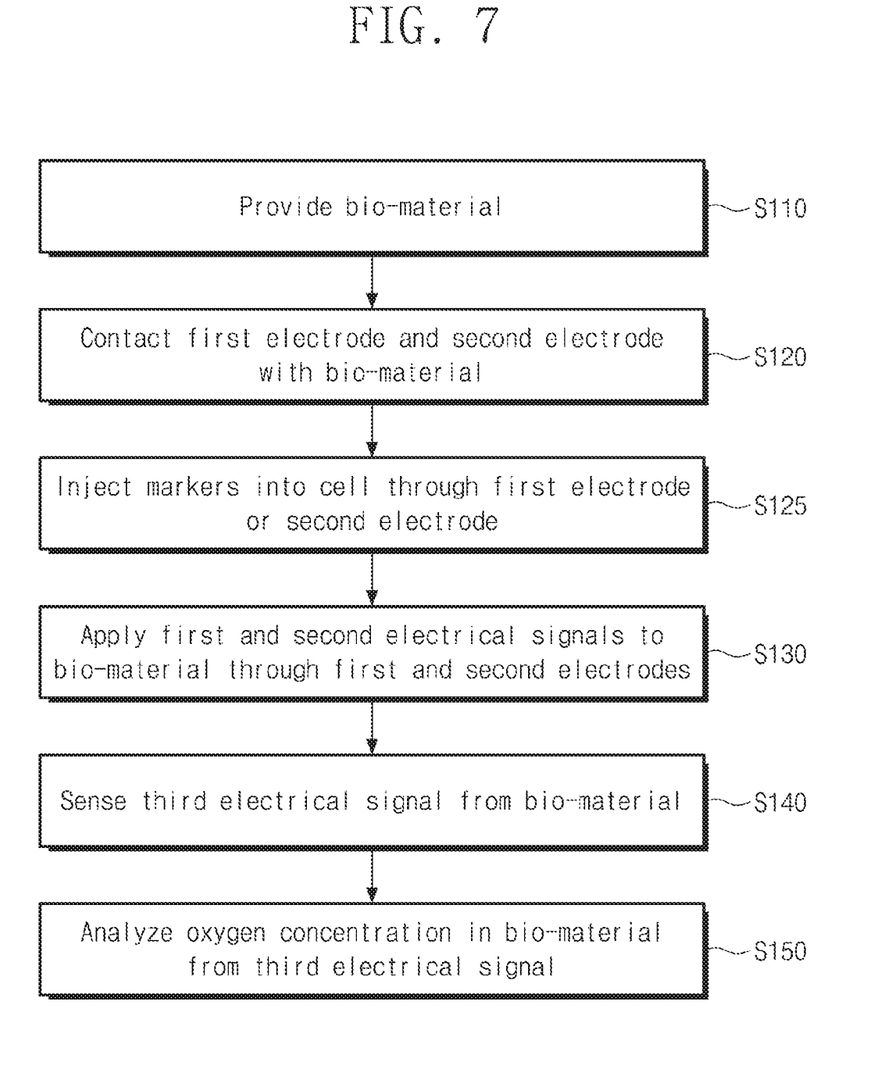
FIG. 7 is a flowchart illustrating a biometric information measurement method according to another embodiment.
Figure 8A:
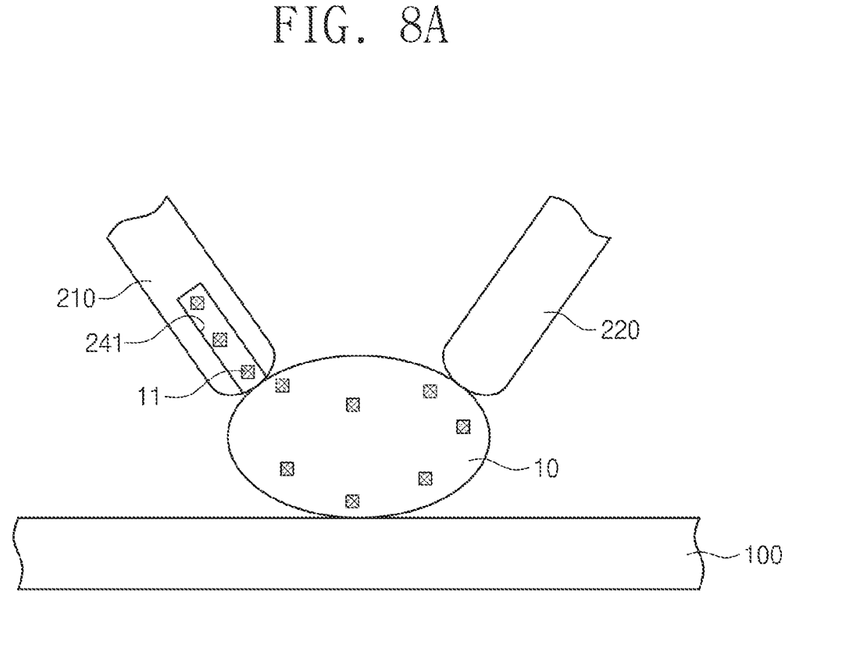
FIG. 8A is a diagram for explaining a biometric information measurement method according to another embodiment.
Figure 8B:
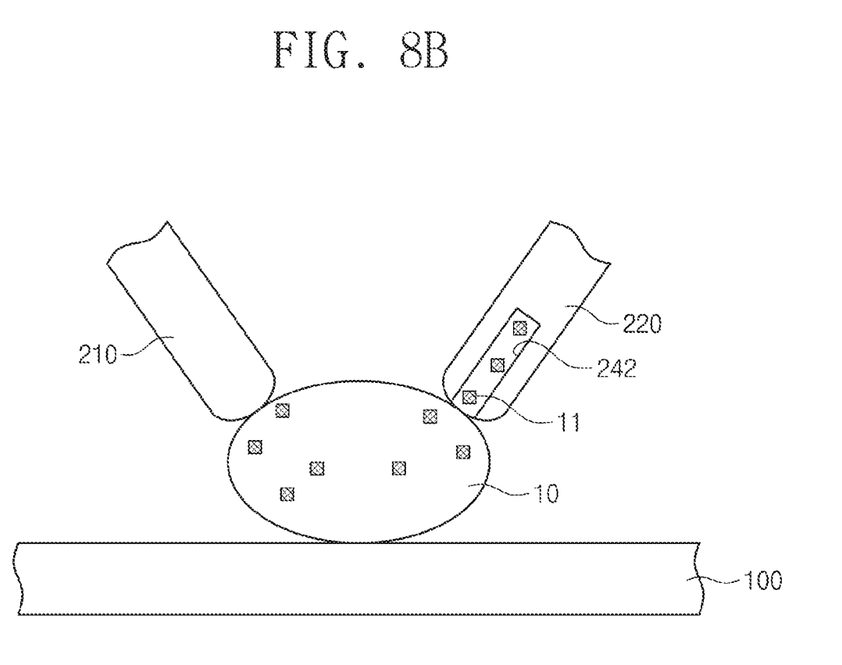
FIG. 8B is a diagram for explaining a biometric information measurement method according to another embodiment.

FIG. 7 is a flowchart illustrating a biometric information measurement method according to another embodiment. FIG. 8A is a diagram for explaining a biometric information measurement method according to another embodiment. FIG. 8B is a diagram for explaining a biometric information measurement method according to another embodiment. The following description will be made with reference to FIG. 2, and the contents overlapping with those described above will be omitted.

Referring to FIGS. 7, 8A, and 8B, the biometric information measurement method of bio-material 10 may include providing the bio-material 10 (S110), contacting the first electrode 210 and the second electrode 220 with the bio-material 10 (S120), injecting the markers 11 into the bio-material 10 through the first electrode 210 or the second electrode 220 (S125), applying first and second electrical signals to the bio-material 10 through the first and second electrodes 210 and 220 (S130), sensing a third electrical signal from the bio-material 10 (S140), and measuring the oxygen concentration in the bio-material 10 from the third electrical signal (S150).

As shown in FIG. 8A, the first electrode 210 may include a first injection unit 241 therein. As another example, the first electrode 210 may be the first injection unit 241. The markers 11 may be provided in the first injection unit 241. The markers 11 may be injected into the bio-material 10 through the first electrode 210. Thereafter, the first electrode 210 may apply a first electrical signal to the bio-material 10.

As shown in FIG. 8B, the second electrode 220 may include a second injection unit 242 therein. The markers 11 may be provided in the second injection unit 242. The markers 11 may be injected into the bio-material 10 through the second electrode 220. Thereafter, the second electrode 220 may apply a second electrical signal to the bio-material 10. As another example, the second electrode 220 may be the second injection unit 242.

The providing of the bio-material 10 (S110), the contacting of the first electrode 210 and the second electrode 220 with the bio-material 10 (S120), and the applying of the first and second electrical signals to the bio-material 10 through the first and second electrodes 210 and 220 (S130) may be substantially the same as those described with reference to FIGS. 2 to 4. The sensing of the third electrical signal from the bio-material 10 (S140) and the measuring of the oxygen concentration in the bio-material 10 from the third electrical signal (S150) may be substantially the same as those described with reference to FIGS. 2 to 6B.

Figure 9:
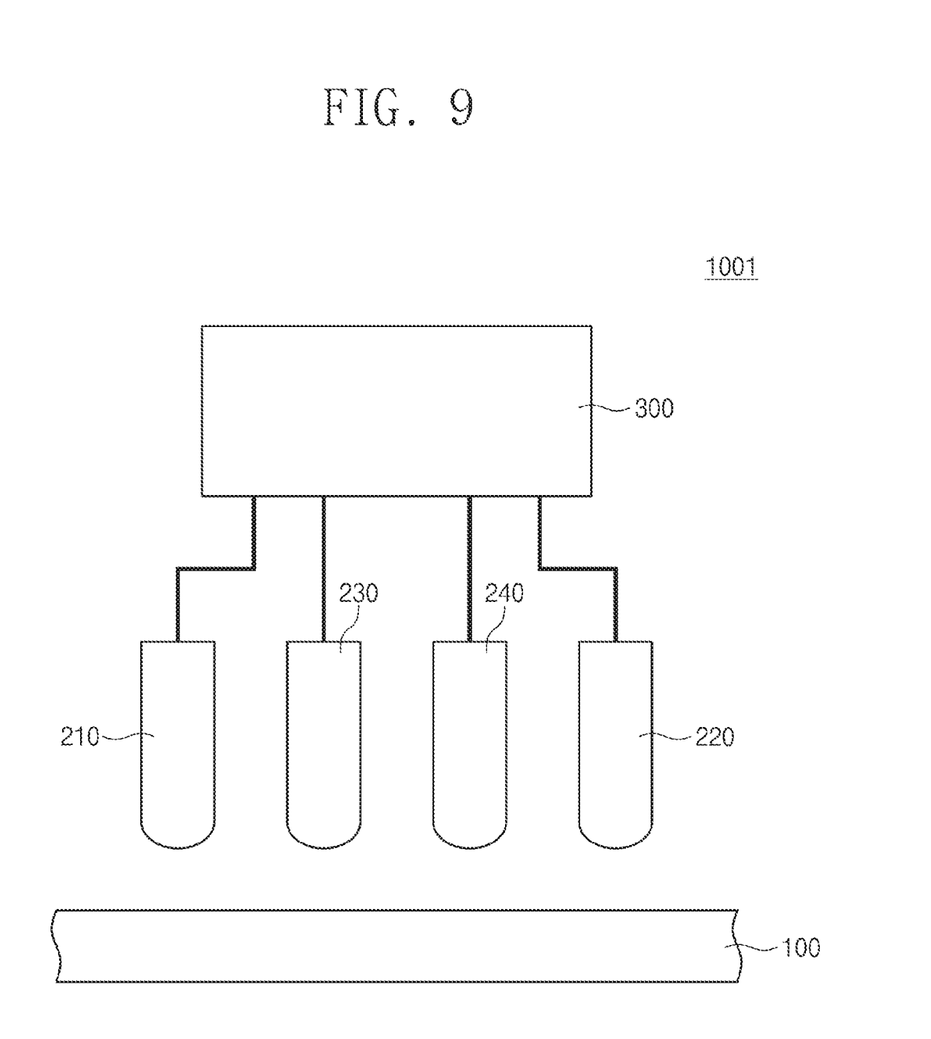
FIG. 9 is a schematic diagram illustrating a biometric information measurement device according to other embodiments.
Figure 10:
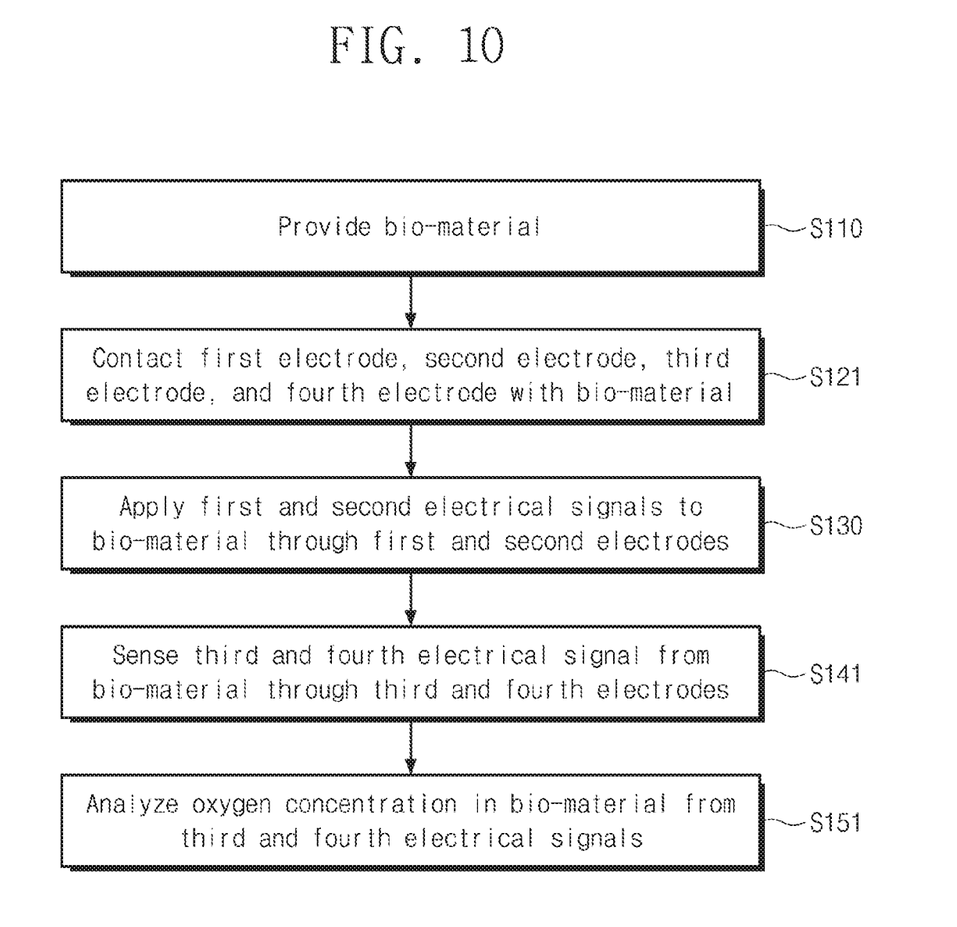
FIG. 10 is a flowchart illustrating a biometric information measurement method according to other embodiments.
Figure 11:
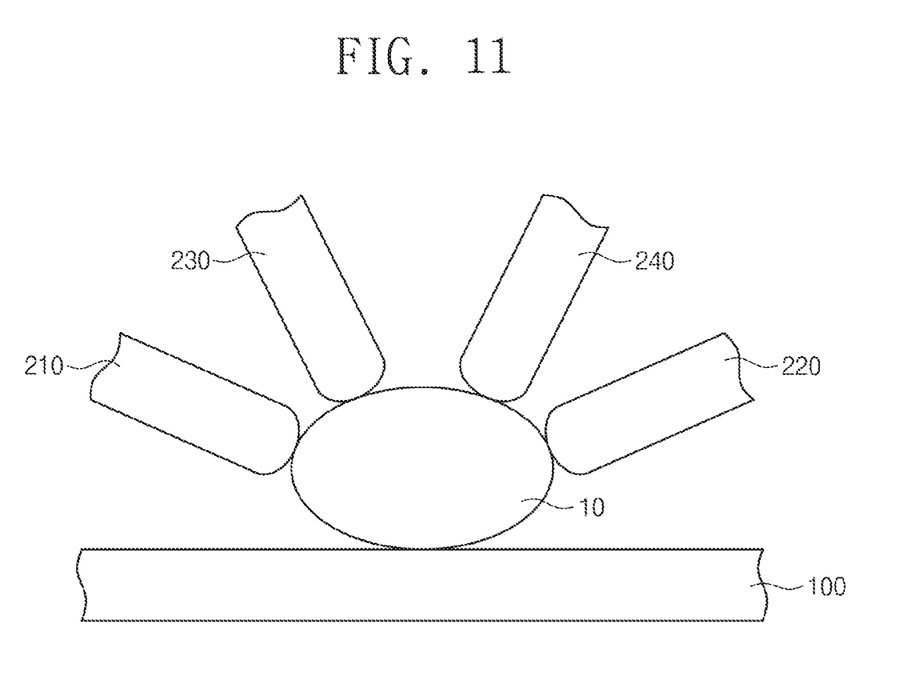
FIG. 11 is a diagram for explaining a biometric information measurement method according to other embodiments.

FIG. 9 is a schematic diagram illustrating a biometric information measurement device according to other embodiments. FIG. 10 is a flowchart illustrating a biometric information measurement method according to another embodiment. FIG. 11 is a diagram for explaining a biometric information measurement method according to another embodiment.

Referring to FIGS. 9, 10, and 11, a biometric information measurement device 1001 may include a plate 100, a first electrode 210, a second electrode 220, a third electrode 230, a fourth electrode 240, and a control unit 300. The first electrode 210, the second electrode 220, the third electrode 230, and the fourth electrode 240 may include a conductive material. The first electrode 210 and the second electrode 220 may function as driving electrodes.

The third electrode 230 and the fourth electrode 240 may function as a sensing electrode. The control unit 300 may be electrically connected to the first electrode 210, the second electrode 220, the third electrode 230, and the fourth electrode 240. For example, the signal applying unit 310 of FIGS. 1A and 1B may be electrically connected to the first electrode 210, the second electrode 220, the third electrode 230, and the fourth electrode 240. The signal receiving unit 320 of FIGS. 1A and 1B may be electrically connected to the first electrode 210, the second electrode 220, the third electrode 230, and the fourth electrode 240.

The bio-material 10 may be provided on the plate 100 (S110). The first electrode 210, the second electrode 220, the third electrode 230, and the fourth electrode 240 may contact the bio-material 10 (S121).

The first and second electrical signals may be applied to the bio-material 10 through the first electrode 210 and the second electrode 220 (S130). For example, the first electrical signal may be applied to the bio-material 10 by using the first electrode 210. The second electrode 220 may apply a second electrical signal to the bio-material 10. The application of the first electrical signal and the application of the second electrical signal may be substantially the same as those described with reference to FIGS. 2 to 4.

An electrical signal may be sensed from the bio-material 10 through the third electrode 230 and the fourth electrode 240 (S141). For example, the third electrode 230 may sense a third electrical signal from the bio-material 10. The third electrical signal may be permittivity or electrical conductivity. The fourth electrode 240 may sense the fourth electrical signal from the bio-material 10. The fourth electrical signal may be permittivity or electrical conductivity. Thus, the fourth electrical signal may be different from the third electrical signal. The third electrical signal and the fourth electrical signal may be transmitted to the signal receiving unit 320. The signal receiving unit 320 may transmit the third electrical signal and the fourth electrical signal to the signal analyzing unit 330 of FIG. 1A or the biometric information analyzing unit 1300 of FIG. 1B.

The oxygen concentration in the bio-material 10 may be measured from the third electrical signal and the fourth electrical signal (S151). The signal analyzing unit 330 of FIG. 1A or the biometric information analyzing unit 1300 of FIG. 1B may analyze the third electrical signal and the fourth electrical signal to calculate the oxygen concentration in the bio-material 10. A fourth electrical signal may be further provided so that the error due to the surface resistance of the bio-material 10 may be reduced. Accordingly, the measurement accuracy of the oxygen concentration in the bio-material 10 may be improved.

According to the inventive concept, biometric information (for example, oxygen concentration) in a cell or tissue may be quantitatively measured. Thus, early detection of disease may be possible.

Although the exemplary embodiments of the inventive concept have been described, it is understood that the inventive concept should not be limited to these exemplary embodiments but various changes and modifications may be made by one ordinary skilled in the art within the spirit and scope of the inventive concept as hereinafter claimed.

What is claimed is:

1. A biometric information measurement method comprising:
providing a bio-material including at least one of cells and tissues;
contacting a first electrode and a second electrode with the bio-material;
applying a first electrical signal and a second electrical signal to the bio-material through the first electrode and the second electrode;
sensing a third electrical signal from the bio-material through the first electrode and the second electrode; and
analyzing an oxygen concentration in the bio-material from the third electrical signal.

2. The method of claim 1, wherein the first electrical signal comprises a current or a voltage, and
wherein the second electrical signal comprises a current or a voltage.

3. The method of claim 1, wherein the contacting of the first electrode with the bio-material comprises penetrating a surface of the bio-material.

4. The method of claim 1, further comprising contacting a third electrode with the bio-material, wherein the sensing of the third electrical signal is performed through the third electrode.

5. The method of claim 4, further comprising:
contacting a fourth electrode with the bio-material; and
sensing a fourth electrical signal from the bio-material through the fourth electrode,
wherein the fourth electrical signal is different from the third electrical signal.

6. A biometric information measurement system comprising a biometric information measurement device including:
a control unit including a signal applying unit and a signal receiving unit;
a first electrode electrically connected to the signal applying unit and the signal receiving unit; and
a second electrode electrically connected to the signal applying unit and the signal receiving unit,
wherein the first electrode is configured to apply a first electrical signal to a bio-material,
wherein the second electrode is configured to apply a second electrical signal to the bio-material,
wherein the signal receiving unit is configured to collect a third electrical signal generated from the bio-material,
wherein the signal receiving unit is configured to collect the third electrical signal through the first electrode and the second electrode, and
wherein the signal applying unit is configured to apply the first electrical signal and the second electrical signal through the first electrode and the second electrode.

7. The system of claim 6, wherein the control unit further comprises a signal analyzing unit,
wherein the signal analyzing unit analyzes an oxygen concentration in the bio-material from the third electrical signal.

8. The system of claim 6, further comprising a biometric information analyzing unit spaced apart from the biometric information measurement device,
   wherein the biometric information analyzing unit analyzes an oxygen concentration in the bio-material from the third electrical signal.

9. The system of claim 6, wherein the first electrode and the second electrode are configured to contact the bio-material.

* * * * *